United States Patent
Yi

(10) Patent No.: US 6,929,144 B2
(45) Date of Patent: Aug. 16, 2005

(54) APPARATUS FOR LOCKING A PRESSURE VESSEL

(75) Inventor: Yong-ik Yi, Seoul (KR)

(73) Assignee: Shinhung Company Ltd., Seoul (KR)

(*) Notice: Subject to any disclaimer, the term of this patent is extended or adjusted under 35 U.S.C. 154(b) by 92 days.

(21) Appl. No.: 10/433,409

(22) PCT Filed: Jun. 27, 2001

(86) PCT No.: PCT/KR01/01094

§ 371 (c)(1),
(2), (4) Date: Nov. 13, 2003

(87) PCT Pub. No.: WO02/45757

PCT Pub. Date: Jun. 13, 2002

(65) Prior Publication Data

US 2004/0069785 A1 Apr. 15, 2004

(30) Foreign Application Priority Data

Dec. 4, 2000 (KR) ........................................ 2000-72839

(51) Int. Cl.⁷ .............................................. B65D 95/00
(52) U.S. Cl. ..................................... 220/318; 220/324
(58) Field of Search ................................ 220/318, 324, 220/323, 316–317, 581, 582, 243, 251; A61L 2/06

(56) References Cited

U.S. PATENT DOCUMENTS

| | | | | | |
|---|---|---|---|---|---|
| 1,316,943 A | * | 9/1919 | Dundon | ...................... | 220/315 |
| 1,929,761 A | * | 10/1933 | Thwaits | ...................... | 220/314 |
| 2,108,238 A | * | 2/1938 | Sterlow | ....................... | 220/314 |
| 2,572,963 A | * | 10/1951 | Wily | ............................ | 220/314 |
| 2,599,072 A | * | 6/1952 | Schweiso | .................... | 220/316 |
| 4,248,160 A | * | 2/1981 | Carney et al. | ......... | 105/377.11 |
| 4,622,902 A | * | 11/1986 | Miller | .................... | 105/377.11 |
| 4,889,056 A | * | 12/1989 | Stewart | .................. | 105/377.11 |
| 4,948,185 A | * | 8/1990 | Miller | ..................... | 292/256.5 |

FOREIGN PATENT DOCUMENTS

| | | |
|---|---|---|
| JP | 52-74696 | 6/1977 |
| JP | 5-9551 | 2/1993 |
| JP | 7-163638 | 6/1995 |
| JP | 7-328101 | 12/1995 |

OTHER PUBLICATIONS

International Search Report, PCT/KR01/01094, dated Oct. 17, 2001, 2 pages.
English translation of JP 5–9551, 5 pages.
English abstract for JP 7–163638, 1 page.
English abstract for JP 7–328101, 1 page.

* cited by examiner

Primary Examiner—Lien M. Ngo
(74) Attorney, Agent, or Firm—Finnegan, Henderson, Farabow, Garrett & Dunner, L.L.P.

(57) ABSTRACT

The invention provides an apparatus for locking a pressure vessel. A locking pins-receiving member is installed on the front portion of said chamber, with locking pins-receiving holes being formed vertically through said locking pins-receiving member. A side of each supporting frame, which supports the door of said vessel, is fastened to the exterior of the door. Both ends of said supporting frame extends beyond the boundary of said door. A shifting member comprises a handle, locking pins, and connecting members connecting said handle to said locking pins. Locking pins are capable of shifting in piercing holes, which are formed at the end part of said supporting frames. Grooves extends longitudinally in a regular length from said pass-through holes towards the center of said supporting frames, such that said connecting members are capable of being inserted therein.

12 Claims, 6 Drawing Sheets

(A)

(B)

(A)

(B)

APPARATUS FOR LOCKING A PRESSURE VESSEL

CROSS REFERENCE TO RELATED APPLICATIONS

This application is a National Phase Application based on PCT/KR01/01094, filed on Jun. 27, 2001, the contents of which are incorporated herein by reference and claims the priority of Korean Patent Application No. 2000/0072839, filed on Dec. 4, 2000, the contents of which are incorporated herein by reference.

This invention relates to a locking device of a pressure vessel. In particular, this invention relates to a locking device of a pressure vessel which hermetically closes the door of the pressure vessel to prevent leakage of inner wet vapors and secure safe sealing such that the pressure in the pressure vessels, such as chambers of sterilizers which sterilize medical apparatus and the like, may be endured.

FIELD OF THE INVENTION

Generally, the chamber of a sterilizer is formed to increase sealing ability for sterilization. A conventional locking device for a sterilizer, for example an invention described in U.S. patent application Ser. No. 774,166, discloses a locking device employing a sliding bolt as a means to lock the door to increase sealing ability of the chamber as shown in FIG. 6 as a representative example.

In the locking device as the above, problems exist where vapors within the chamber leak from the boundaries of the door distant from the locking device and lower performance or the door may be opened when the operator unintentionally moves the handle while passing by the door, which may inflict injury upon the operator.

Therefore, the object of the present invention is to provide a locking device of a pressure vessel which can increase sealing ability in boundaries of the door distant from the locking device and also improve locking characteristics by supporting the door which seals the chamber by means of support frames provided on the outside surface of the door.

SUMMARY OF THE INVENTION

To achieve the foregoing object, there is provided a locking device of a pressure vessel having a locking pin receiving member which is installed on one side of the front of the said chamber and in which a locking pin receiving hole is formed in the vertical direction, a spindle receiving member which is installed in front of said chamber in a position opposite said locking pin receiving member with an opening of said chamber in the front of said chamber in between and in which a hole is formed in the vertical direction, a support frame of which a portion of one side is fixed on the outer surface of said door and of which both ends extend beyond the boundary limited by the outer circumference of said door and of which one end is rotatably coupled with said spindle receiving member by a spindle and thereby said door is rotated about said spindle and opens and closes said chamber and a shifting member having a handle, a locking pin which can shift vertically within said support frame, and a connecting member which connects said handle and said locking pin, wherein a pass-through hole which can be interconnected with the hole of said locking pin receiving hole, and a groove which extends in a longitudinal direction by a predetermined length from said pass-through hole to the center of said support frame, are formed on the other end of said support frame, and the connecting member of said shifting member can be inserted into said groove.

The cross-section of said locking pin may be oval shaped or a similar shape, or may be a shape where one end of the locking pin is protruded. In the other end of said support frame, a resilient spring portion, which applies resilience on said locking pin, is further installed and may improve tie locking performance.

In the locking device of the pressure vessel of the present invention, the door is supported by the support frame, and thereby has the effect of increasing the sealing of the boundaries of the door distant from the locking device. Also, the locking pin may be manufactured in various shapes. As one example, the cross-section of the locking pin may be manufactured to be an oval or similar shape, having the advantage of not needing protrusions. In the case of protrusion formed on the locking pin, instead of forming the locking pin into an oval shape, a protrusion may be formed on the bottom of the locking pin and thereby simplifying the manufacturing process. In addition, in the case of a resilient spring portion being formed in the portion where the locking pin is inserted into the locking pin receiving hole, there is the advantage where even when an operator mistakenly pulls the handle during the pressurized sterilization state of the chamber, the door does not fully open due to the resilience of the spring and thereby the accident of wet vapor spouting out to the operator may be prevented.

| <Description of the reference numbers > | |
| --- | --- |
| 20: chamber | 21: locking pin receiving member |
| 22: locking pin receiving hole | 23: spindle receiving member |
| 26: door | 28: support frame |
| 30: spindle | 32: handle |
| 33: shifting member | 36: locking pin |
| 38: protrusion | 39: connecting member |
| 46: resilient spring portion | 48: groove |
| 50: pass-through hole | |

DETAILED DESCRIPTION OF THE PREFERRED EMBODIMENTS

Figure 1:
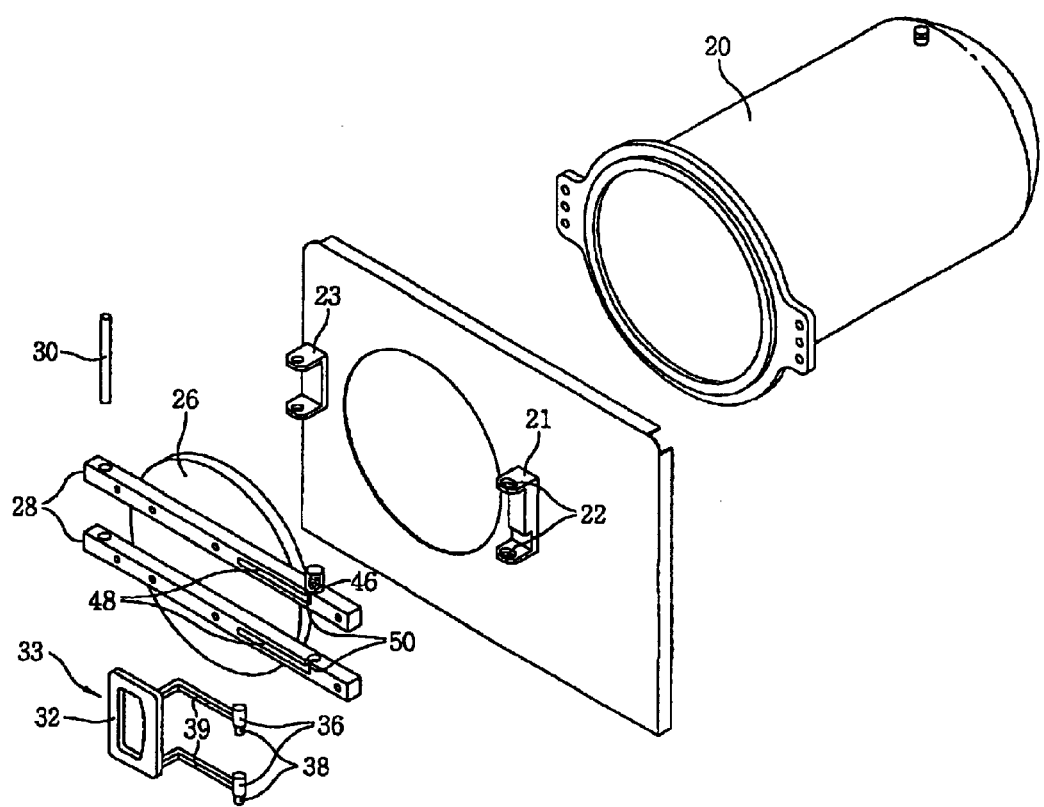
FIG. 1 is an exploded view of the locking device of the pressure vessel according to the present invention.
Figure 2:
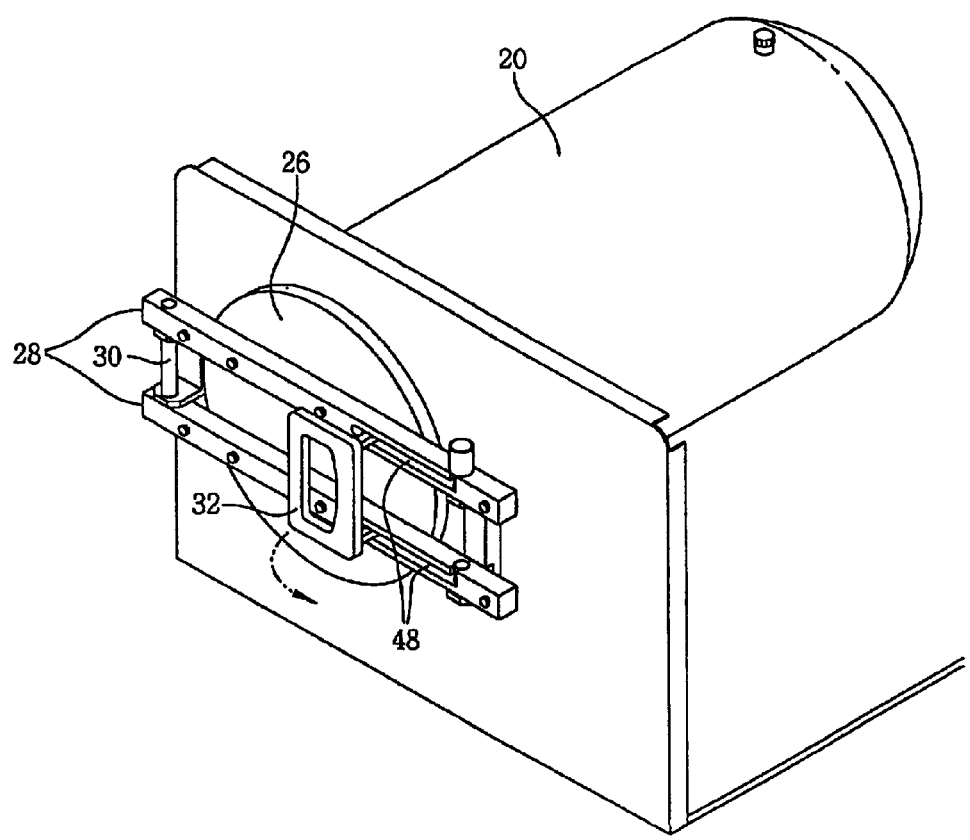
FIG. 2 is a perspective view of the locked state of the locking device of the pressure vessel according to the present invention.

FIG. 1 is an exploded view of the locking device of the pressure vessel according to the present invention, and FIG. 2 is a perspective view of the locking device of the pressure vessel of the present invention in a locked state, and the preferred embodiment of this invention is described hereinafter with reference to the above drawings.

In the present invention, as shown in FIG. 1 and FIG. 2, to prevent gases, such as wet vapors having a high temperature and high pressure produced from inside the chamber (20) during sterilization, from leakage to the outside of the chamber (20), two support frames (28) are provided on the outside of the door (26). Not only do said support frames (28) serve to prevent the door (26) from opening when the door (26) is locked, but also serve to prevent leakage of interior gases that occur when the boundary of the door is pushed even when the door is not opened.

One end of said support frame(28) is rotatably fixed on the spindle receiving member(23) fixed on the front of the chamber by a spindle(30), and thereby the door(26) is opened only by the rotational motion about the spindle(30).

On the locking pin receiving member (21) fixed on the front of the sterilizer which may be reached by the other end of said support frame (28), a locking pin receiving hole (22) is formed, and the locking pin (36) of the shifting member (33), described hereinafter, is inserted in hole (22) and thereby said door (26) may be locked.

On the other end of said support frame (28), a pass-through hole (50) formed in the vertical direction such that it may be inter-connected to the locking pin receiving hole (22) of the locking pin receiving member (21), and a groove (48) which extends in a longitudinal direction by a predetermined length from said pass-through hole (50) to the center of said support frame (28) are formed, and the locking pin (36) formed on one end of said shifting member (33) is inserted within said pass-through hole (50) such that it may shift in the vertical direction, and a connecting member (39) connected to said locking pin (36) is installed such that when the shifting member (33), composed of the handle (32), locking pin (36) and connecting member (39), rotates about said locking pin by a predetermined angle, the connecting member may enter and leave said groove (48).

On the other end of said shifting member(33), a handle (32) is formed to make rotation of said locking pin(36) and connecting member(39) easier, and as in the locked state as shown in FIG. 2, because said connecting member(39) is inserted into said groove(48), the handle(32) is also positioned near the door(26), and therefore in this locked state, the connecting member or handle prevent unintentional opening by the operator.

Meanwhile, at the inside boundary portion of the door where the inside surface of the door(26) closes on to the front of the chamber, a resilient member made from heat-resistant material is provided, and in the locked state said resilient member is in a compressed state to some degree, and therefore the door may be completely sealed, and in particularly, in pressure vessels used in sterilizers, said resilient member is made from material harmless to the human body such as silicon.

Corresponding to the movement of the handle(32) of the shifting member(33), the locking pin(36) rotates in the same spot and the connecting member(39) rotates about the locking pin(36). Said locking pin is made from a high-strength material with enough strength to avoid damage from maximum pressure within the chamber during operation.

Figure 4:
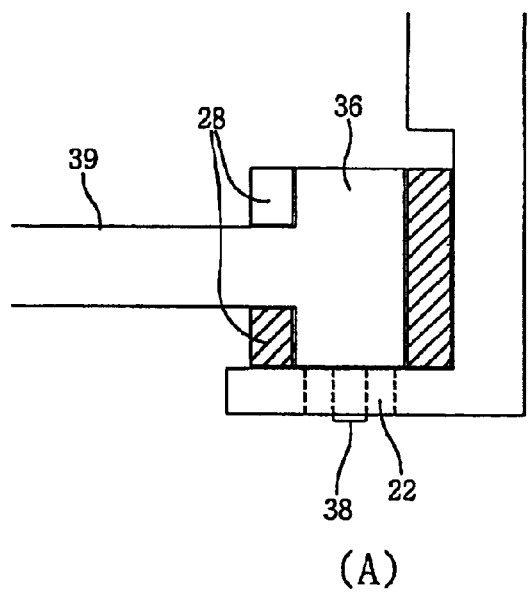
FIG. 4(A) is a sectional view showing the locking pin and the surrounding at a state when the handle is pulled forward in the case where the locking pin of the locking device of the pressure vessel according to the present invention is round and a protrusion is formed on a portion of the bottom of the locking pin.
FIG. 4(B) is a sectional view showing the locking pin and the surrounding at a state when the handle is closed to the door in the case where the locking pin of the locking device of the pressure vessel according to the present invention is round and a protrusion is formed on a portion of the bottom of the locking pin.
Figure 4:
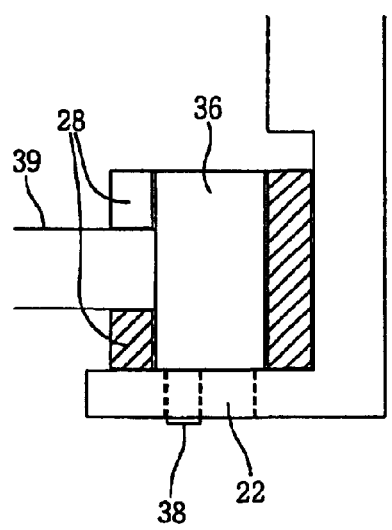

When the handle (32) is pulled forward, the tight coupled state of the locking pin (36) and locking pin receiving hole (22) as shown in FIG. 4(B), is changed to a free movement state as shown in FIG. 4(A), and thereby the door(26) is loosely freed.

In this state, the connecting member(39) and locking pin(36) can be easily shifted in an upward direction along the pass-through hole(50).

When the connecting member(39) and locking pin(36) are shifted, said locking pin(36) separates from the locking pin receiving hole(22), and at this point, when the handle(32) is pulled again, the door(26) is completely opened.

In the locking device of a pressure vessel formed as the above, the portion of the locking pin (36) which is inserted into the locking pin receiving hole (22), may be formed as a protrusion (38). Said protrusion constitutes a portion of locking pin, and the locking pin of the case where there is no protrusion, which inserts into the locking pin receiving hole, becomes the protrusion. In the case where the protrusion (38) is formed on the locking pin (36), only the protrusion (38) is inserted into said locking pin receiving hole (22). In this case, the cross-section of said locking pin receiving hole (22) is oval shape. The releasing and locking of the door (26) by the protrusion (38) is respectively depicted in FIG. 4(A) and FIG. 4(B).

As another preferred embodiment of the locking pin, the cross-section of the locking pin(36) is oval or similar shape and the case of a protrusion not being formed on one end thereof is described hereinafter with reference to FIG. 5 and focused on the different points in comparison to the foregoing preferred embodiments.

Figure 5:
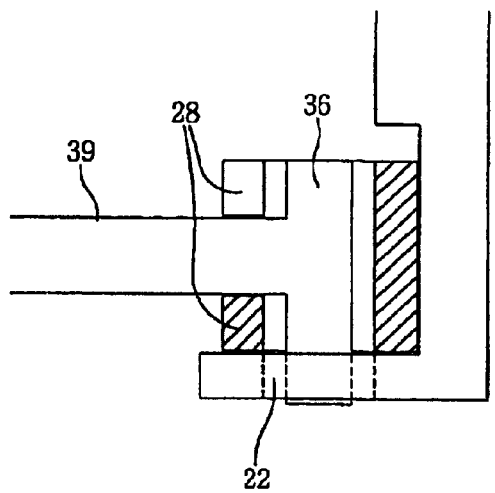
FIG. 5(A) is a sectional view showing the locking pin and the surrounding at a state when the handle is pulled forward in the case where the locking pin of the locking device of the pressure vessel according to the present invention is oval or a similar shape.
FIG. 5(B) is a sectional view showing the locking pin and the surrounding at a state when the handle is closed to the door in the case where the locking pin of the locking device of the pressure vessel according to the present invention is oval or a similar shape.
Figure 5:
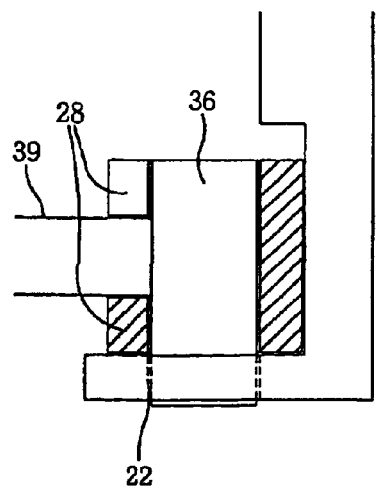
Figure 6:
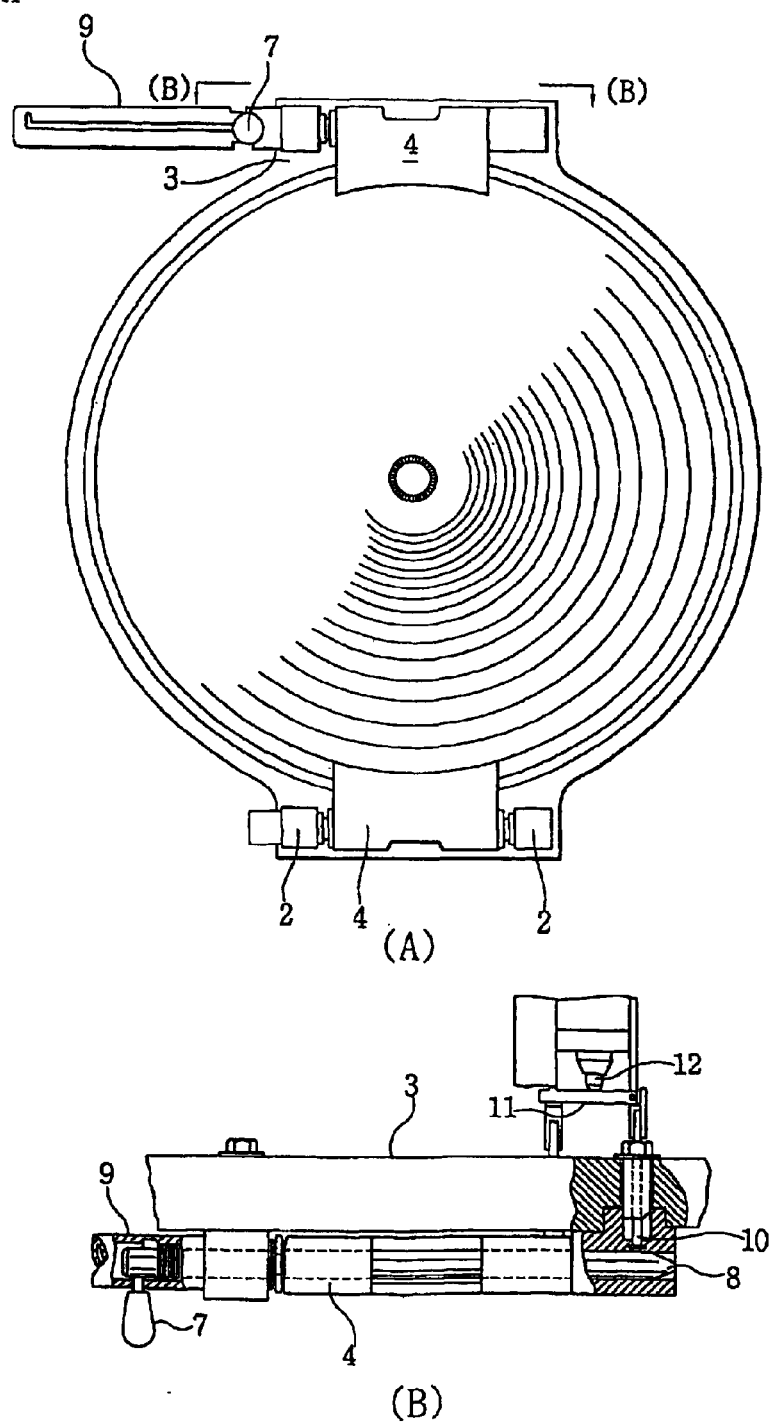
FIG. 6(A) is a front view of the conventional locking device of a pressure vessel.
FIG. 6(B) is a sectional view of FIG. 6(A) along line (B)—(B).

FIG. 5 is an enlarged sectional view, which depicts the operation state of the locking pin receiving hole(22) and locking pin(36), where FIG. 5(A) shows the released state and FIG. 5(B) shows the locked state. Although in FIG. 5, the cross-section of the locking pin(36) and locking pin receiving hole(22) is depicted as an oval shape, in case the shape is one which allows tight inter-coupling between the locking pin and the locking pin receiving hole(22) due to the rotational motion of the locking pin(36), any shape may be used.

Figure 3:
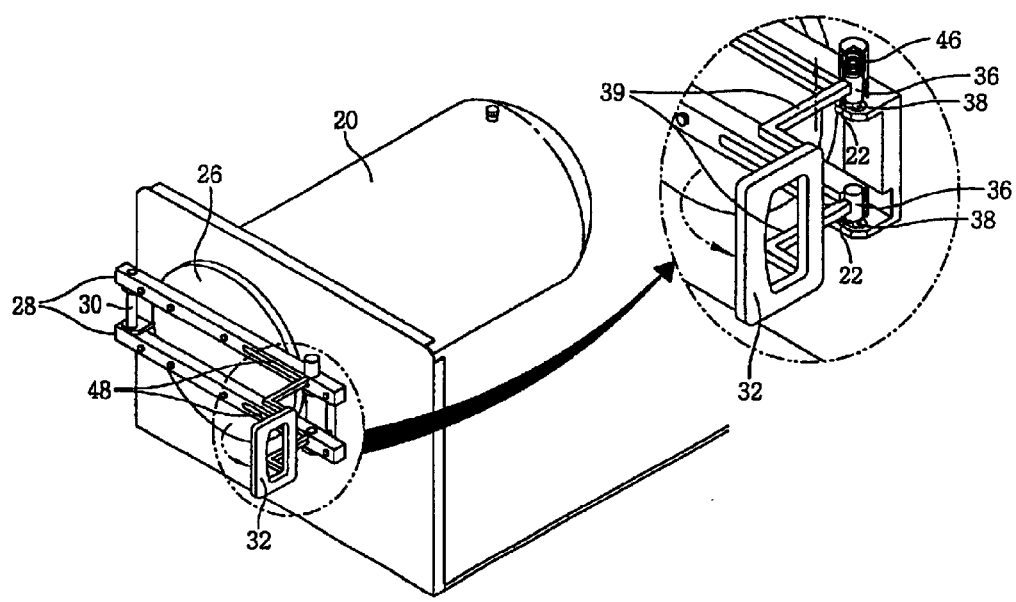
FIG. 3 is a partial sectional view of the locking device of the pressure vessel according to the present invention.

As depicted in FIG. 1 to FIG. 3, in the support frame of the locking device of the pressure vessel according to the present invention, a resilient spring portion (46) may be installed. FIG. 3 is a sectional view of the support frame with the resilient spring portion (46) installed. The locking device of a pressure vessel having the support frame including the resilient spring portion (46) as component is described hereinafter. As shown in the figures, a one side of said pass-through hole (50) of said support frame (28), the resilient spring portion (46) is installed in the upward direction of the locking pin (36). By employing the resilient spring portion (46), when the handle (32) is casually let go after being shifted, the locking spin (36) is subject to a downward force by action of the resilience of the spring in the resilient spring portion (46) and accordingly, the locking pin (36) maintains the state of being inserted within the locking pin receiving hole (22). In the locking device of the present invention constructed as the above, because the locking pin (36) inserted in the locking pin receiving hole (22) is released only when the handle (32) is forcefully shifted in the upward direction with a force exceeding the resilience of the spring after being pulled forward, the handle (32) may not be easily shifted even when the handle is unintentionally pulled, for example by loose clothing of the operator, during a pressurized operation state, and therefore the door is not opened.

Accordingly, the locking device has the advantage of preventing cases where the door(26) is pushed due to the pressure and gases such as hot wet vapors produced in the inside are spouted on to the operator.

Although the present preferred embodiment has been described with an example of two support frames, the present invention is not limited to the case where the number of support frames are two, and an arbitrary number of support frames of more than two may be used depending on the pressure of the medium accommodated within the pressure vessel.

The locking device of the present invention has been described as basically being a locking device for a sterilizer. However, the locking device may be used as a locking device for any pressure vessel in which the interior pressure is higher than the exterior pressure.

What is claimed is:

1. A locking device of a pressure vessel provided with a door which seals a chamber comprising:
    a locking pin receiving member which is installed on one side of the front of said chamber and in which a locking pin receiving hole is formed in the vertical direction,
    a spindle receiving member which is installed in the front of said chamber in a position opposite said locking pin receiving member with an opening of said chamber in between and in which a hole is formed in the vertical direction,
    a support frame of which a portion of one side is fixed on the outer surface of said door and of which both ends extend beyond the boundary limited by the outer circumference of said door and of which one end is rotatably couple with said spindle receiving member by a spindle and thereby said door is rotated about said spindle and opens and closes said chamber, and
    a shifting member having a handle, a locking pin which can shift vertically within said support frame, and a connecting member which connects said handle and said locking pin,
    wherein a pass-through hole which can be inter-connected with the hole of said locking pin receiving hole, and a groove which extends in a longitudinal direction by a predetermined length from said pass-through hole to the center of said support frame, are formed on the other end of said support frame, and the connecting member of said shifting member can be inserted into said groove.

2. The locking device of a pressure vessel of claim 1, wherein one end of said locking pin is a protrusion.

3. The locking device of a pressure vessel of claim 1, wherein said locking pin has an oval cross-section or similar in shape.

4. The locking device of a pressure vessel of claim 1, wherein on the other end of said support frame is further installed a resilient spring portion which applies resilience on said locking pin.

5. The locking device of a pressure vessel of claim 1, wherein said pressure vessel is a sterilizer vessel which sterilizes apparatus such as medical apparatus.

6. The locking device of a pressure vessel of claim 4, wherein said pressure vessel is a sterilizer vessel which sterilizes apparatus such as medical apparatus.

7. The locking device of a pressure vessel of claim 2, wherein on the other end of said support frame is further installed a resilient spring portion which applies resilience on said locking pin.

8. The locking device of a pressure vessel of claim 3, wherein on the other end of said support frame is further installed a resilient spring portion which applies resilience on said locking pin.

9. The locking device of a pressure of vessel of claim 2, wherein said pressure vessel is a sterilizer vessel which sterilizes apparatus such as medical apparatus.

10. The locking device of pressure vessel of claim 3, wherein said pressure vessel is a sterilizer vessel which sterilizes apparatus such as medical apparatus.

11. The locking device of a pressure vessel of claim 7, wherein said pressure vessel is a sterilizer vessel which sterilizes apparatus such as medical apparatus.

12. The locking device of a pressure vessel of claim 8, wherein said pressure vessel is a sterilizer vessel which sterilizes apparatus such as medical apparatus.

* * * * *

UNITED STATES PATENT AND TRADEMARK OFFICE
CERTIFICATE OF CORRECTION

PATENT NO. : 6,929,144 B2
DATED : August 16, 2005
INVENTOR(S) : Yong-ik Yi

It is certified that error appears in the above-identified patent and that said Letters Patent is hereby corrected as shown below:

Column 5,
Line 47, "couple" should read -- coupled --.

Column 6,
Line 36, "pressure of vessel" should read -- pressure vessel --.
Line 39, "of pressure" should read -- of a pressure --.

Signed and Sealed this

Eighteenth Day of April, 2006

JON W. DUDAS
*Director of the United States Patent and Trademark Office*